US00PP37209P3

(12) United States Plant Patent
Kolster

(10) Patent No.: US PP37,209 P3
(45) Date of Patent: Jan. 13, 2026

(54) ***COTINUS* PLANT NAMED 'Kolmagipur'**

(50) Latin Name: *Cotinus coggygria*
Varietal Denomination: Kolmagipur

(71) Applicant: Kolster Holding B.V., Boskoop (NL)

(72) Inventor: Peter Rudolf Kolster, Boskoop (NL)

(73) Assignee: KOLSTER HOLDING BV, Boskoop (NL)

( * ) Notice: Subject to any disclaimer, the term of this patent is extended or adjusted under 35 U.S.C. 154(b) by 0 days.

(21) Appl. No.: 19/057,187

(22) Filed: Feb. 19, 2025

(65) Prior Publication Data

US 2025/0268114 P1 Aug. 21, 2025

(30) Foreign Application Priority Data

Feb. 21, 2024 (QZ) ..... PBR 20240500

(51) Int. Cl.
*A01H 5/12* (2018.01)
*A01H 5/00* (2018.01)
*A01H 6/00* (2018.01)

(52) U.S. Cl.
USPC ..... Plt./226
CPC ..... *A01H 6/00* (2018.05); *A01H 5/00* (2013.01)

(58) Field of Classification Search
USPC ..... Plt./226, 216
CPC ... A01H 5/12; A01H 5/00; A01H 5/04; A01H 6/00
See application file for complete search history.

(56) References Cited

U.S. PATENT DOCUMENTS

PP14,120 P2 * 9/2003 Kolster ..... A01H 6/00
Plt./226

OTHER PUBLICATIONS

CPVO Plant Breeder's Application No. 2024/0500 for 'Kolmaglpur' dated Feb. 21, 2024, 20 pages total. (Year: 2024).*
Florisol Plante ornamentale 2023, retrieved on May 14, 2025 at https://www.florisol.ro/sites/default/files/Oferta%20plante-ornamentale-pt.-buchete-2024-1612.pdf, 3 pp. (Year: 2023).*
Kolster BV Cutflowers New Varieties 2023, retrieved on May 14, 2025 at https://easyfairsassets.com/sites/166/2023/01/Verkleind-bestand-7-MB-New-varieties-2023-KOLST2202-Brochure-Snijbloemen-A4-8HR-gecomprimeerd.pdf, 16 pp. (Year: 2023).*
Magical Garden Plants Catalogue 2022, retrieved on May 14, 2025 at https://www.genesis-plantmarketing.co.uk/wp-content/uploads/2023/01/Catalogue-Magical-Garden-Plants-2022.pdf, cover page, pp. 1, 3, 6-7, 10-11, 50-51, 9 total pages. (Year: 2022).*
Google English translation retrieved on May 14, 2025 at https://www.google.com/search?q=translation&sca_esv=d86c9b659a2f6e13&source=hp&ei=quAkale8GqH-iLMP0bqSkAw&iflsig=ACkRmUkAAAAAaCTuuoJRT . . . , 3 pp.) (Year: 2025).*

* cited by examiner

*Primary Examiner* — June Hwu
(74) *Attorney, Agent, or Firm* — Penny J. Aguirre

(57) ABSTRACT

A new cultivar of *Cotinus* plant named 'Kolmagipur' that is characterized by its dark purple colored foliage, its straight and strong branches, its abundance of stems, and its small sized leaves.

2 Drawing Sheets

Botanical classification: *Cotinus coggygria.*
Variety denomination: 'Kolmagipur'.

CROSS-REFERENCE TO A RELATED APPLICATION

This application claims priority to European Community Plant Variety Office (CPVO) Plant Breeder's Rights Application No. 2024/0500 filed on Feb. 21, 2024, under 35 U.S.C. 119(f), the entire contents of which is incorporated by reference herein. The information for the plant breeders' rights application was received directly from the Inventor.

BACKGROUND OF THE INVENTION

The present invention relates to a new and distinct cultivar of *Cotinus coggygria* and will be referred to hereafter by its cultivar name, 'Kolmagipur'. 'Kolmagipur' is a new cultivar grown for use as a landscape plant.

The new cultivar of *Cotinus* arose from a breeding program conducted by the Inventor in Boskoop, The Netherlands with the goal of developing an *Cotinus* cultivar with dark color foliage in combination with desirable growth habits.

The new cultivar arose from a cross made by the Inventor in Boskoop, The Netherlands in June of 2015 between *Cotinus* cultivars 'Royal Purple' (not patented) as the female parent and 'Young Lady' (not patented) as the male parent. The Inventor selected 'Kolmagipur' as a single unique plant amongst the seedlings that resulted from the above cross in July of 2018.

Asexual propagation of the new cultivar was first accomplished under the direction of the inventor by stem cuttings in August of 2018 in Boskoop, The Netherlands. Asexual propagation by stem cuttings and tissue culture using meristamic tissue has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Kolmagipur' as a unique cultivar of *Cotinus*.

1. 'Kolmagipur' exhibits dark purple colored foliage.
2. 'Kolmagipur' exhibits straight and strong branches.
3. 'Kolmagipur' exhibits an abundance of stems.
4. 'Kolmagipur' exhibits small sized leaves.

The female parent of 'Kolmagipur' differs from 'Kolmagipur' in having crooked and less upright branches, foliage that is lighter purple in color, and leaves that are larger in size. The male parent of 'Kolmagipur' differs from 'Kolmagipur' in having foliage that is green in color that turns orange-red-yellow in color in fall, and leaves that are larger in size. 'Kolmagipur' can be compared to the *Cotinus coggygria* cultivars 'Kolmarfo' (not patented) and 'Kolcot' (U.S. Plant Pat. No. 14,120). 'Kolmarfo' is similar to 'Kolmagipur' in having purple colored foliage and straight branches. 'Kolmarfo' differs from 'Kolmagipur' in having larger sized leaves, foliage that is lighter purple in color, and less abundant stems. 'Kolcot' is similar to 'Kolmagipur' in having straight branches. 'Kolcot' differs from 'Kolmagipur' in having larger sized leaves that are green in color.

BRIEF DESCRIPTION OF THE DRAWINGS

The accompanying colored photographs illustrate the overall appearance and distinct characteristics of the new *Cotinus*. The plants in the photographs are 3-years in age as grown outdoors in a field in Boskoop, The Netherlands.

The photograph in FIG. 1 illustrates the overall plant habit and foliage coloration of 'Kolmagipur' in summer.

Figure 1:
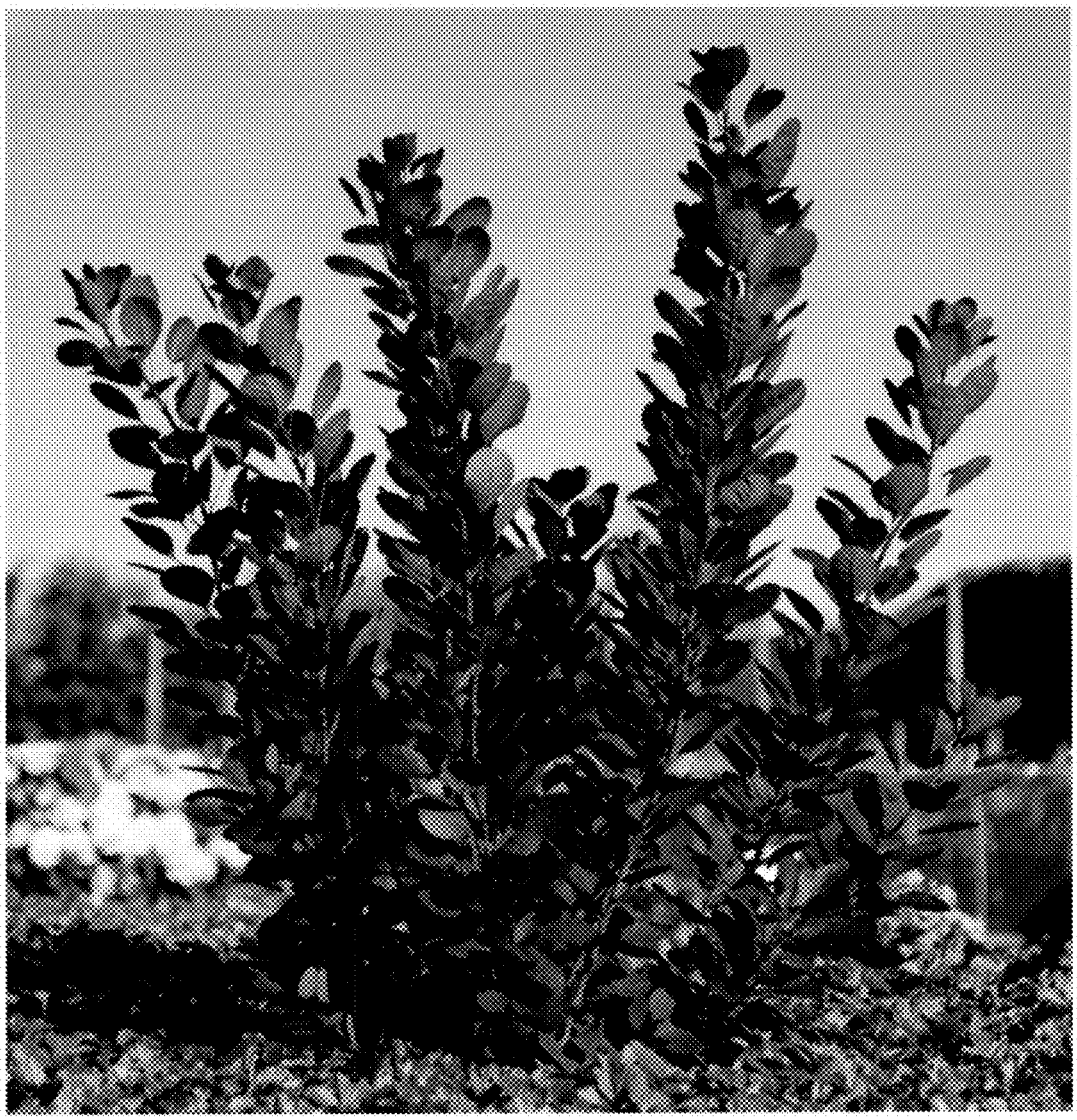
Figure 2:
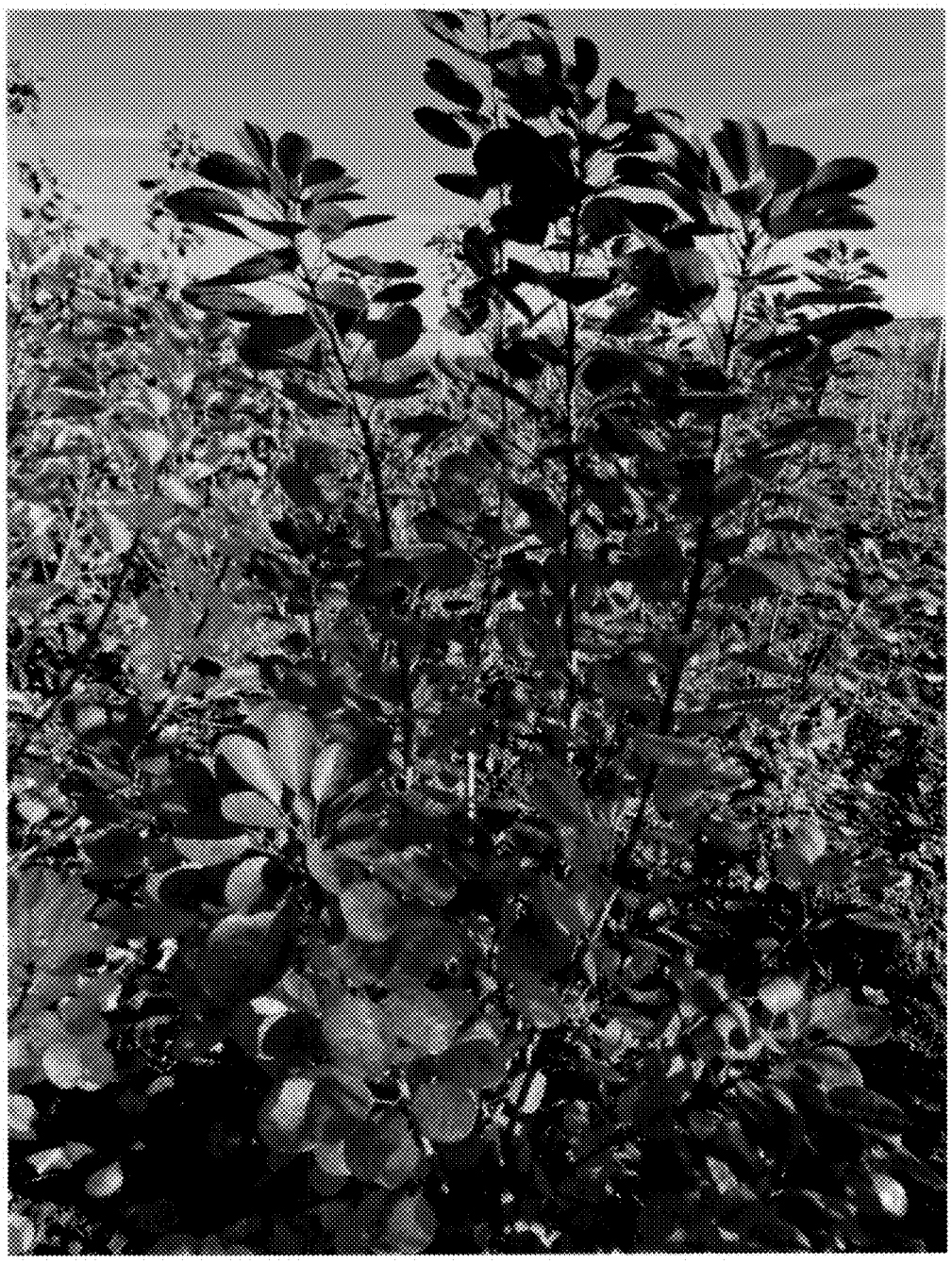

The photograph in FIG. 2 provides a view of the fall foliage of 'Kolmagipur'.

The colors in the photographs are as close as possible with the digital photography techniques utilized and the color values cited in the detailed botanical description accurately describe the colors of the new *Cotinus*.

DETAILED BOTANICAL DESCRIPTION

The following is a detailed description of 3 year-old plants of the new cultivar as grown outdoors in a field in Boskoop, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—Mid-May to late May in The Netherlands.

*Plant habit*.—Upright with strong and straight branches.

*Height and spread*.—Plants 1 year in age from a bare root shrub will reach 1.5 m in 2 years, can reach 2.5 m in height and 1 m in width in the landscape.

*Cold hardiness*.—At least in U.S.D.A. Zone 4.

*Diseases and pests*.—No susceptibility or resistance to diseases or pests have been observed.

*Root description*.—Fibrous.

*Propagation*.—Stem cuttings and tissue sulture (preferred).

*Root development*.—Root initiate in 3 months, young rooted plant is produced in 1 year from a rooted cutting.

*Growth rate*.—Moderate.

Branch description:

*Branch shape*.—Round.

*Branch strength*.—Moderately strong.

*Branching*.—Main; 5, lateral; 10.

*Branching aspect*.—Held in an average angle of 40° (varying between 25° and 60°).

*Branch color*.—Young; 183B, waxy layer N187B, mature; 175D, older bark; N200B and N200C.

*Branch size*.—Main; 37 cm in length, 6 mm in diameter, lateral; 5.2 cm in length, 2 mm in diameter.

*Branch surface*.—Glossy, covered with a matte waxy layer, and pubescent.

*Internode length*.—Main; 9 mm, lateral; 3.5 mm.

Foliage description:

*Leaf shape*.—Broadly elliptic to oblong.

*Leaf division*.—Simple.

*Leaf base*.—Short attenuate.

*Leaf apex*.—Rounded.

*Leaf fragrance*.—None.

*Leaf venation*.—Pinnate, upper surface 185B, lower surface 187B to 187C.

*Leaf margins*.—Entire and slightly undulate.

*Leaf arrangement*.—Alternate.

*Leaf attachment*.—Petiolate.

*Leaf surface*.—Both surfaces smooth and glabrous, matte to very slightly glossy.

*Leaf size*.—Average of 4.6 cm in length, 3.1 cm in width.

*Leaf quantity*.—Average of 35 per lateral branch.

*Leaf color*.—Young and mature upper and lower surface; a blend of N186C and 200A. fall upper surface; primarily N34A, fall lower surface; 162A and suffused with N34A.

*Petioles*.—1 cm in length, 1 mm in diameter, surfaces are smooth and glabrous, slightly glossy, medium strength, both surfaces 187B in color.

*Stipules*.—Absent.

Inflorescence description:

*Inflorescence type*.—Terminal panicle.

*Inflorescence size*.—Average of 9.5 cm in length and 5.9 cm in width.

*Peduncles*.—8.4 cm in length, 1.25 mm in diameter, held in a vertical angle, moderately strong, 187B in color, surfaces are glabrous, smooth, and glossy.

*Pedicels*.—8 mm in length, 0.3 mm in diameter, held in a 30° angle, strong, N186B in color, surfaces are slightly glossy and pubescent.

*Flower buds*.—2 mm in length, 1.5 mm in diameter, broadly elliptic in shape, surface is smooth, glabrous, and matte, color is 187C, immature sepals N186B.

*Flower fragrance*.—Faint, slightly spicy.

*Lastingness of flowers*.—10 days, self-cleaning.

*Flower quantity*.—Average of 1,500 per inflorescence.

*Flower type*.—Rotate.

*Flower aspect*.—Upright on pedicels.

*Flower size*.—About 4.5 mm in diameter and 2.5 mm in depth.

*Petals*.—4 to 5, cruciform, 1 whorl, 2 mm in length, 1.5 mm in width, ovate in shape, acute apex, cuneate base, entire margins, both surfaces smooth, glabrous, and matte, color; when opening upper surface 161C, top and margins 178B, when opening lower surface 181B, when full open upper surface 178B, base 161B, when fully open lower surface 181A to 181B.

*Sepals*.—Campanulate in arrangement, 5, 1 whorl, 1.75 mm in length, 0.75 mm in width, fused into a campanulate shape, acute apex, entire margins, both surfaces smooth and glabrous, upper surface color; 147A, top N186C, lower surface color; 200B.

Reproductive organs:

*Pistils*.—1, 1.2 mm in length, style; 1 mm in length, 144C in color, stigma; club-shaped, 0.2 mm in width, 8A in color, ovary; 144C in color.

*Stamens*.—4, filament; 1.5 mm in length, 187B in color, anther; 3 mm in length, 183A in color, pollen; moderate, 11A in color.

*Fruit and seed*.—None observed to date.

It is claimed:

1. A new and distinct cultivar of *Cotinus* plant named 'Kolmagipur' as herein illustrated and described.

* * * * *